(12) United States Patent
Fujikura (10) Patent No.: US 7,678,044 B2
(45) Date of Patent: Mar. 16, 2010

(54) ENDOSCOPIC DEVICE (75) Inventor: Tetsuya Fujikura, Saitama (JP)

(73) Assignees: Fujifilm Corporation, Tokyo (JP); SRJ Corporation, Tochigi (JP)

( * ) Notice: Subject to any disclaimer, the term of this patent is extended or adjusted under 35 U.S.C. 154(b) by 950 days.

(21) Appl. No.: 11/079,133

(22) Filed: Mar. 15, 2005

(65) Prior Publication Data
US 2005/0215856 A1 Sep. 29, 2005

(30) Foreign Application Priority Data
Mar. 16, 2004 (JP) ............................. 2004-074872
Nov. 4, 2004 (JP) ............................. 2004-321224

(51) Int. Cl.
*A61B 1/00* (2006.01)

(52) U.S. Cl. ..................... 600/115; 600/114; 600/116; 600/132; 600/156; 600/157; 600/158; 600/159; 604/96.01; 604/101.01; 604/101.02; 604/101.04; 604/103.05

(58) Field of Classification Search ......... 600/115–116; 604/96.01–103.11
See application file for complete search history.

(56) References Cited

U.S. PATENT DOCUMENTS

| 4,040,413 | A | | 8/1977 | Ohshiro |
| 4,815,450 | A | * | 3/1989 | Patel .......................... 600/115 |
| 5,144,848 | A | * | 9/1992 | Uenishi et al. ............. 73/866.5 |
| 5,188,596 | A | * | 2/1993 | Condon et al. ........... 604/103.1 |
| 5,243,967 | A | | 9/1993 | Hibino |
| 6,126,635 | A | | 10/2000 | Simpson et al. |
| 6,764,441 | B2 | * | 7/2004 | Chiel et al. ................. 600/115 |
| 2003/0220544 | A1 | * | 11/2003 | Chang ........................ 600/156 |
| 2005/0059931 | A1 | * | 3/2005 | Garrison et al. ........ 604/101.04 |

FOREIGN PATENT DOCUMENTS

JP 51-11689 1/1976
JP 2004-329720 11/2004

* cited by examiner

*Primary Examiner*—Matthew J Kasztejna
(74) *Attorney, Agent, or Firm*—Young & Thompson (57) ABSTRACT

A first balloon is fitted to an insertion portion of an endoscope and a second balloon is fitted to an insertion aid member. An end connector of a tube is connected to a balloon control device that supplies and sucks air into and from the first balloon and the second balloon. A duct that communicates with the first balloon, a duct that communicates with the second balloon, and a duct that communicates with a clearance between the insertion portion and the insertion aid member are formed in the end connector.

6 Claims, 6 Drawing Sheets

ENDOSCOPIC DEVICE

BACKGROUND OF THE INVENTION

1. Field of the Invention

The present invention relates to an endoscopic device, and more particularly to an endoscopic device that alternately inserts an insertion portion of an endoscope and an insertion aid member to insert the insertion portion into an alimentary canal in a deep part such as small intestine or large intestine for observation.

2. Related Art

When an insertion portion of an endoscope is inserted into an alimentary canal in a deep part such as small intestine, complex bending of intestine prevents a force from being transmitted to a tip of the insertion portion in simple insertion of the insertion portion, and insertion into a deep part is difficult. For example, surplus bending or flection in the insertion portion prevents the insertion portion from being further inserted into the deep part. Thus, a method is proposed for inserting an insertion portion of an endoscope covered with an insertion aid member into a body cavity, and guiding the insertion portion with the insertion aid member to prevent surplus bending or flection of the insertion portion.

Japanese Patent Application Laid-open No. 51-11689 describes an endoscopic device including a first balloon at a tip of an insertion portion of an endoscope, and a second balloon at a tip of an insertion aid member (also referred to as an over tube or a sliding tube). This endoscopic device alternately inserts the insertion portion and the insertion aid member while repeating expansion and contraction of the first balloon and the second balloon, thereby allowing the insertion portion to be inserted into a deep part of intestine with complex bending.

SUMMARY OF THE INVENTION

In the conventional endoscopic device, a connector on the side of the endoscope that communicates with the first balloon and a connector on the side of the insertion aid member that communicates with the second balloon are individually connected to a balloon control device. Further, a lubricant supply device such as a syringe is connected to a connector for a duct through which a lubricant is injected between the insertion portion and the insertion aid member. Thus, the conventional endoscopic device includes many connectors and takes trouble in connecting the connectors, and may cause connection errors of the connectors.

The invention has been achieved in view of the above described. circumstances, and has an object to provide an endoscopic device that facilitates connection of a connector and causes no connection errors.

In order to achieve the above described object, a first aspect of the invention provides an endoscopic device, comprising: an endoscope having a first balloon at a tip of an insertion portion thereof; an insertion aid member that is placed over the insertion portion of the endoscope to guide insertion of the insertion portion into a body cavity, and has a second balloon at a tip thereof; and a balloon control device that controls supply and suction of a fluid into and from the first balloon and the second balloon, wherein a first duct that communicates with the first balloon, a second duct that communicates with the second balloon, and a third duct through which a lubricant is supplied between the insertion portion and the insertion aid member are connected to one connecter, and the connector is connected to the balloon control device.

According to the first aspect of the invention, the three ducts are connected to the balloon control device via one connector, thereby reducing the number of connectors as compared with the case where a connector is provided for each duct. This facilitates connection of the connector, and eliminates connection errors of the connector.

In order to achieve the above described object, a second aspect of the invention provides an endoscopic device, comprising: an endoscope having a first balloon at a tip of an insertion portion thereof; an insertion aid member that is placed over the insertion portion of the endoscope to guide insertion of the insertion portion into a body cavity, and has a second balloon at a tip thereof; and a balloon control device that controls supply and suction of a fluid into and from the first balloon and the second balloon, wherein the balloon control device is provided inside an external device to which a connector portion of the endoscope is connected, a first duct that communicates with the first balloon, a second duct that communicates with the second balloon, and a third duct through which a lubricant is supplied between the insertion portion and the insertion aid member are connected to the connecter portion of the endoscope, and the connector portion is connected to the external device to connect at least the first duct and the second duct to the balloon control device.

According to the second aspect of the invention, the connector portion of the endoscope is connected to the external device to simultaneously connect the three ducts to the balloon control device. This further facilitates connection of the connector. The external device is a light source device or a processor for the endoscope, and the connector portion of the endoscope is a so-called light guide connector or an electric connector.

In order to achieve the above described object, a third aspect of the invention provides an endoscopic device, comprising: an endoscope having a first balloon at a tip of an insertion portion thereof; an insertion aid member that is placed over the insertion portion of the endoscope to guide insertion of the insertion portion into a body cavity, and has a second balloon at a tip thereof; and a balloon control device that controls supply and suction of a fluid into and from the first balloon and the second balloon, wherein a first duct that communicates with the first balloon, a second duct that communicates with the second balloon, and a third duct through which a lubricant is supplied between the insertion portion and the insertion aid member are connected to a connecter portion of the endoscope connected to an external device, and the connector portion and the balloon control device are connected by a tube to connect at least the first duct and the second duct to the balloon control device.

According to the third aspect of the invention, the three ducts are connected to the connector portion of the endoscope, and thus the connector portion and the balloon control device are simply connected by the tube to allow the three ducts to be connected to the balloon control device. This facilitates connection of the connector, and eliminates connection errors of the connector.

In a fourth aspect of the invention according to any one of the first to third aspects, the third duct is connected to a lubricant injection device via the connector according to the first aspect, or the connector portion of the endoscope according to the second or third aspect.

In the endoscopic device according to the invention, the first duct that communicates with the first balloon, the second duct that communicates with the second balloon, and the third duct through which the lubricant is supplied are connected to the balloon control device via one connecter, or the three ducts are connected to the connector portion of the endoscope connected to the external device and then connected to the balloon control device. This facilitates connection to the balloon control device, and eliminates connection errors.

DETAILED DESCRIPTION OF THE PREFERRED EMBODIMENTS

Figure 1:
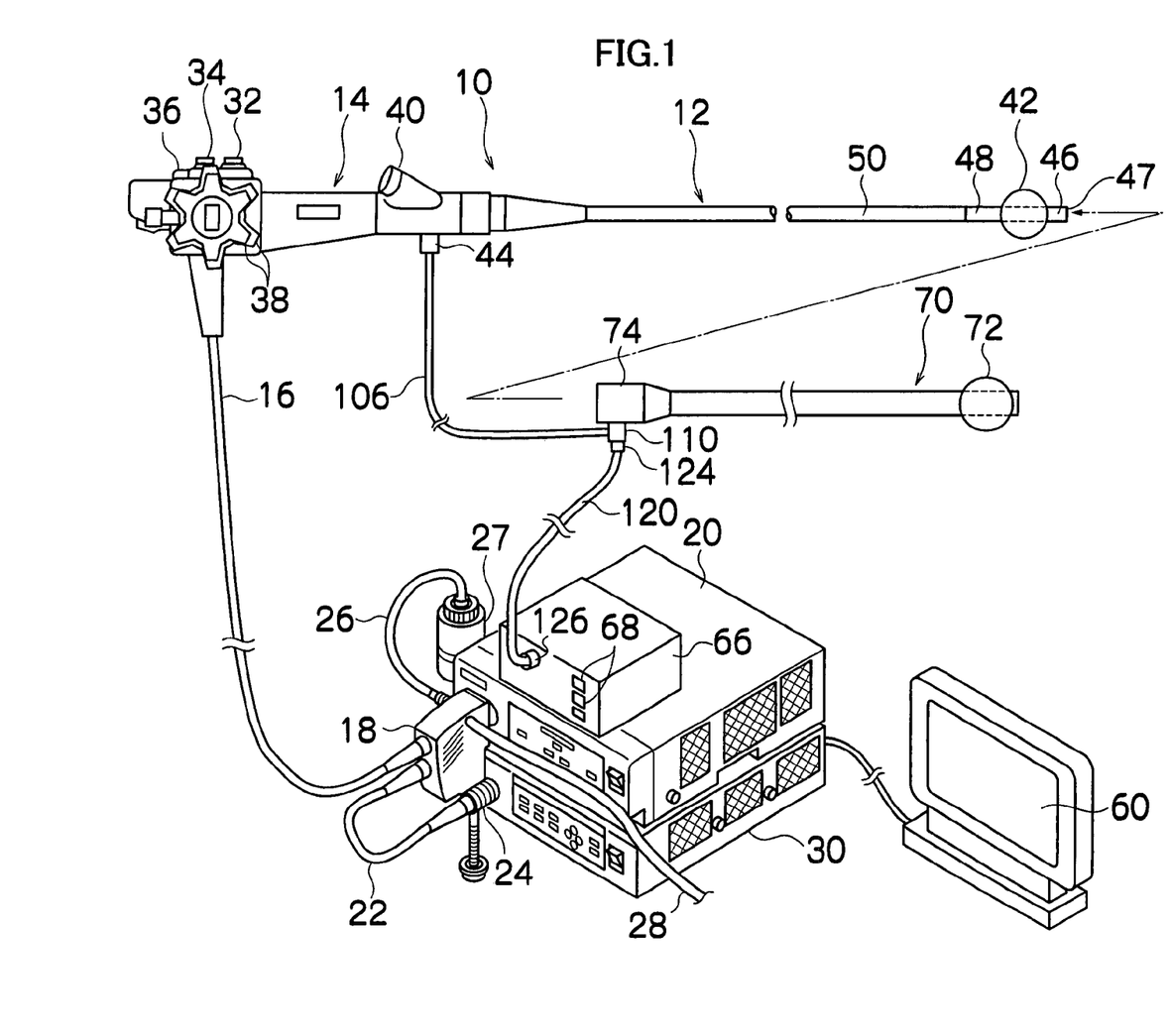
FIG. 1 is a system configuration diagram of an endoscopic device according to the invention.

Now, preferred embodiments of an endoscopic device according to the invention will be described with reference to the accompanying drawings. FIG. 1 is a system configuration diagram of an embodiment of the endoscopic device. As shown in FIG. 1, the endoscopic device mainly includes an endoscope 10, a light source device 20, a processor 30, and a balloon control device 66.

The endoscope 10 includes an insertion portion 12 to be inserted into a body cavity, and a hand operation portion 14 connected to the insertion portion 12. A universal cable 16 is connected to the hand operation portion 14, and a Light Guide (hereinafter referred as LG) connector 18 is provided at a tip of the universal cable 16. The LG connector 18 is removably connected to the light source device 20 to allow illumination light to be transmitted to a below described illumination optical system 54 (see FIG. 2). An electric connector 24 is connected to the LG connector 18 via a cable 22, and the electric connector 24 is removably connected to the processor 30. A tube 26 for feeding air or water and a tube 28 for suction are connected to the LG connector 18.

On the hand operation portion 14, an air/water feed button 32, a suction button 34, and a shutter button 36 are provided side by side, and a pair of angle knobs 38 and a forceps insertion portion 40 are provided. A supply/suction port 44 for supplying a fluid into a below described first balloon 42 or sucking the fluid from the first balloon 42 is also provided in the hand operation portion 14. An example using air as a fluid will be described below, but other fluids such as an inert gas or water may be used.

On the other hand, the insertion portion 12 includes a tip 46, a bending portion 48, and a soft portion 50, and the bending portion 48 is remotely bent by rotating the pair of angle knobs 38 provided on the hand operation portion 14. This allows a tip surface 47 of the tip 46 to be directed to a predetermined direction.

Figure 2:
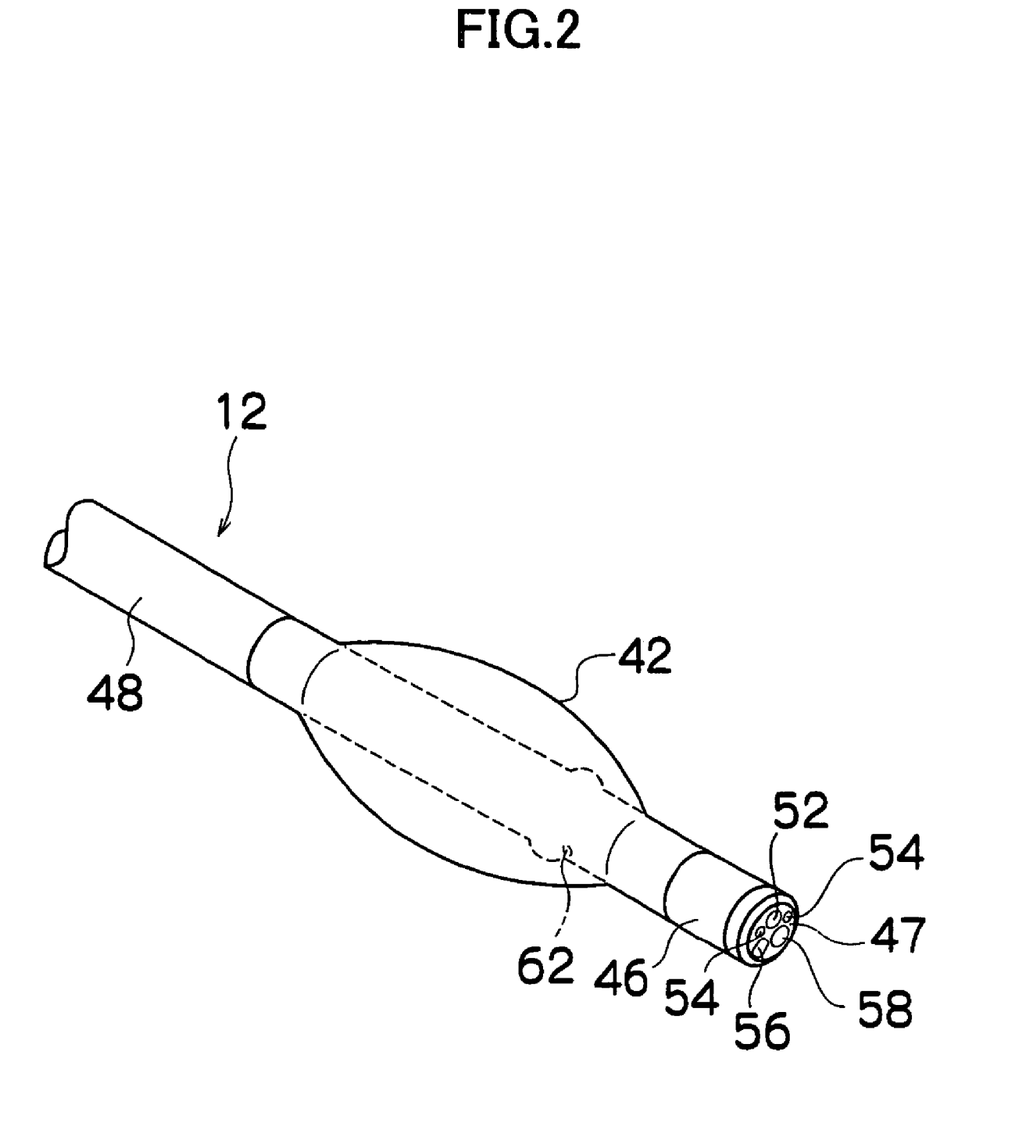
FIG. 2 is a perspective view of a tip of an insertion portion in FIG. 1.

As shown in FIG. 2, an observation optical system 52, illumination optical systems 54, an air/water feed nozzle 56, and a forceps opening 58 are provided in the tip surface 47 of the tip 46. A CCD (not shown) is provided behind the observation optical system 52, and a signal cable is connected to a substrate that supports the CCD. The signal cable is inserted through the insertion portion 12, the hand operation portion 14, and the universal cable 16, extended to the electric connector 24, and connected to the processor 30 in FIG. 1. Thus, an observation image captured by the observation optical system 52 in FIG. 2 is formed on a light receiving surface of the CCD and converted into an electric signal. Then, the electric signal is output to the processor 30 in FIG. 1 via the signal cable, and converted into a video signal. This causes an observation image to be displayed on a monitor 60 connected to the processor 30.

An emission end of a light guide (not shown) is provided behind the illumination optical systems 54 in FIG. 2. The light guide is inserted through the insertion portion 12, the hand operation portion 14, and the universal cable 16 in FIG. 1. Then, an incident end of the light guide is connected to a light guide bar 19 (see FIG. 3) of the LG connector 18. Thus, the light guide bar 19 of the LG connector 18 is connected to the light source device 20 to cause the illumination light from the light source device 20 to be transmitted to the illumination optical systems 54 via the light guide and emitted from the illumination optical systems 54.

Figure 3:
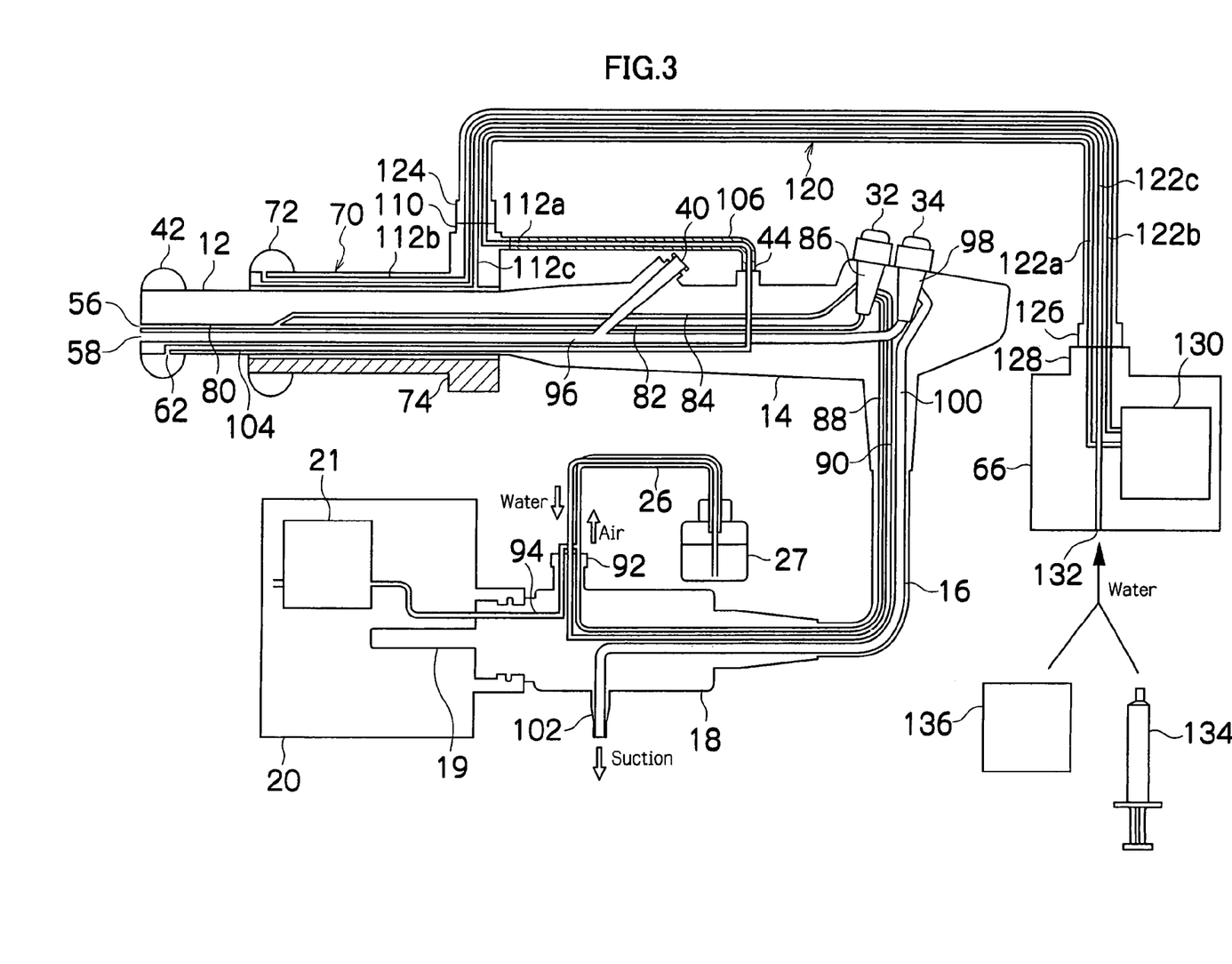
FIG. 3 is a schematic configuration diagram of ducts for a fluid in the endoscopic device.

FIG. 3 is a configuration diagram of ducts for a fluid in the endoscopic device.

As shown in FIG. 3, an air/water feed tube 80 is connected to the air/water feed nozzle 56. The air/water feed tube 80 is branched into an air feed tube 82 and a water feed tube 84, and the air feed tube 82 and the water feed tube 84 each are connected to a valve 86 provided in the hand operation portion 14. To the valve 86, an air supply tube 88 and a water supply tube 90 are connected, and the air/water feed button 32 is mounted. In a state where the air/water feed button 32 protrudes, the air feed tube 82 communicates with the air supply tube 88, and the air/water feed button 32 is pushed to cause the water feed tube 84 to communicate with the water supply tube 90. An air vent (not shown) is formed in the air/water feed button 32, and the air supply tube 88 communicates with outside air via the air vent.

The air supply tube 88 and the water supply tube 90 are inserted through the universal cable 16, and extended to a water feed connector 92 of the LG connector 18. The tube 26 is removably connected to the water feed connector 92, and a tip of the tube 26 is connected to a water storage tank 27. Then, the water supply tube 90 communicates with the water storage tank 27 below a liquid level, and the air supply tube 88 communicates with the water storage tank 27 above the liquid level.

An air tube 94 is connected to the water feed connector 92, and the air tube 94 communicates with the air supply tube 88. The air tube 94 communicates with an air pump 21 in the light source device 20 by the LG connector 18 being connected to the light source device 20. Therefore, when the air pump 21 is driven to feed air, the air is fed to the air supply tube 88 via the air tube 94. This air escapes outside via the air vent (not shown) when the air/water feed button 32 is not operated. Then, an operator closes the air vent to cause the air in the air supply tube 88 to be fed to the air feed tube 82, and injected from the air/water feed nozzle 56. When the air/water feed button 32 is pushed, the air supply tube 88 and the air feed tube 82 are blocked to cause the air supplied to the air tube 94 to be supplied onto the liquid level of the water storage tank 27. This increases internal pressure of the water storage tank 27 to feed water to the water supply tube 90. Then, the water is injected from the air/water feed nozzle 56 via the water feed tube 84. Thus, the water or air is injected from the air/water feed nozzle 56 and sprayed onto the observation optical system 52 to clean the observation optical system 52.

On the other hand, a forceps tube 96 is connected to the forceps opening 58. The forceps tube 96 is branched to communicate with the forceps insertion portion 40 and a valve 98.

Thus, a treatment tool such as forceps is inserted from the forceps insertion portion 40 to lead the treatment tool out of the forceps opening 58. To the valve 98, a suction tube 100 is connected, and the suction button 34 is mounted. In a state where the suction button 34 protrudes, the suction tube 100 communicates with outside air, and the suction button 34 is pushed to connect the suction tube 100 and the forceps tube 96. The suction tube 100 is extended to a suction connector 102 of the LG connector 18, and the tube 28 (see FIG. 1) is connected to the suction connector 102 to cause the suction tube 100 to communicate with an unshown suction device. Therefore, the suction button 34 is pushed in a state where the suction device is driven, thereby allowing a lesion area or the like to be sucked from the forceps opening 58.

A first balloon 42 made of an elastic body such as rubber is fitted to an outer peripheral surface near the tip of the insertion portion 12. As shown in FIG. 2, the first balloon 42 is formed into a substantially cylindrical shape with narrowed opposite ends. The first balloon 42 is fitted in such a manner that the insertion portion 12 is inserted through the first balloon 42 and placed in a desired position, and then the opposite ends of the first balloon 42 are secured to the insertion portion 12. The first balloon 42 is expandable, and expands into a substantially spherical shape or contracts to stick to the outer peripheral surface of the insertion portion 12.

An air vent 62 is formed in the outer peripheral surface of the insertion portion 12 to which the first balloon 42 is fitted. The air vent 62 is connected to the supply/suction port 44 provided in the hand operation portion 14 via a tube 104 shown in FIG. 3. One end of a tube 106 is connected to the supply/suction port 44, and the other end of the tube 106 is connected to a connector 110 of a below described insertion aid member 70.

A length of the tube 106 is such that the insertion aid member 70 is restricted before a tip of the insertion aid member 70 comes into contact with the first balloon 42 when the insertion aid member 70 is slid toward the tip of the insertion portion 12.

On the other hand, the insertion aid member 70 is formed into a cylindrical shape, has an inner diameter slightly larger than an outer diameter of the insertion portion 12, and has sufficient flexibility. A second balloon 72 made of latex is fitted near the tip of the insertion aid member 70. The second balloon 72 is formed into a substantially cylindrical shape with narrowed opposite ends, and fitted with the insertion aid member 70 being passed therethrough. The second balloon 72 expands into a substantially spherical shape by air being supplied thereinto or contracts to stick to an outer peripheral surface of the insertion aid member 70 by air being sucked therefrom.

A hard grip 74 is provided at a base end of the insertion aid member 70, and the insertion portion 12 is inserted from the grip 74. The connector 110 protrudes from an outer peripheral surface of the grip 74.

Three ducts 112a, 112b and 112c are connected to the connector 110. The duct 112a is connected to an opening formed in a side surface of the connector 110. Then, the tube 106 is connected to the opening to cause the duct 112a to communicate with the first balloon 42. The duct 112b communicates with the second balloon 72, and the duct 112c communicates with an inner peripheral surface of the insertion aid member 70. The ducts 112a to 112c may have configurations through which a fluid flows, and may be formed by, for example, forming a through hole in the grip 74 of the insertion aid member 70, or sticking a tube to the inner peripheral surface or the outer peripheral surface of the insertion aid member 70. The shape of the connector 110 and the layout of the ducts 112a to 112c in the connector 110 are not limited, and for example, an end surface of the connector 110 may be formed into an oval shape, and the ducts 112a to 112c may be placed in a line. Alternatively, the end surface of the connector 110 may be formed into a circular shape, and the ducts 112a to 112c may be placed so as to form a regular triangle.

An end connector 124 of a tube 120 is connected to the connector 110. Three ducts 122a, 122b and 122c are formed in the tube 120, and the end connector 124 is connected to the connector 110 to cause the ducts 122a to 122c to communicate with the ducts 112a to 112c, respectively.

The other end connector 126 of the tube 120 is connected to a connector 128 of the balloon control device 66. This causes the duct 122a and the duct 122b to communicate with an air pump 130 in the balloon control device 66. Thus, the air pump 130 is driven to feed and suck air into and from the duct 122a and the duct 122b. The duct 122a communicates with the first balloon 42 via the duct 112a of the insertion aid member 70, the tube 106, and the tube 104, and the duct 122b communicates with the second balloon 72 via the duct 112b. Therefore, the balloon control device 66 allows the first balloon 42 and the second balloon 72 to expand and contract.

On the other hand, the duct 122c communicates with a lubricant injection port 132 of the balloon control device 66 by the end connector 126 being connected to the connector 128. The duct 122c communicates with a clearance between the insertion aid member 70 and the insertion portion 12 via the duct 112c. Thus, a lubricant such as water is injected from the lubricant injection port 132 of the balloon control device 66 to allow the lubricant to be supplied into the clearance between the insertion aid member 70 and the insertion portion 12. As an injection device of the lubricant, a syringe 134 or a pump 136 is used.

In the endoscopic device configured as described above, the three ducts 122a to 122c are connected to the end connector 126 of the tube 120 connected to the balloon control device 66. The duct 122a is a first duct that communicates with the first balloon 42, the duct 122b is a second duct that communicates with the second balloon 72, and the duct 122c is a third duct for the lubricant. Thus, the three ducts 122a to 122c are collectively connected to one end connector 126 to facilitate connection to the balloon control device 66. Further, the number of the connectors is reduced to eliminate connection errors of the connector.

According to the embodiment, the three ducts 122a to 122c are collectively connected to one end connector 126, and thus one tube 120 only is connected to the balloon control device 66. This prevents a plurality of connection tubes from being entangled in operation of the endoscope 10 or the insertion aid member 70, thereby improving operability.

Further, according to the embodiment, the base end of the insertion aid member 70 and the hand operation portion 14 of the endoscope 10 are connected by the tube 106, and thus the tube 106 serves as a stopper in insertion of the insertion aid member 70 to prevent the tip of the insertion aid member 70 from coming into contact with the first balloon 42 of the insertion portion 12.

Figure 4:
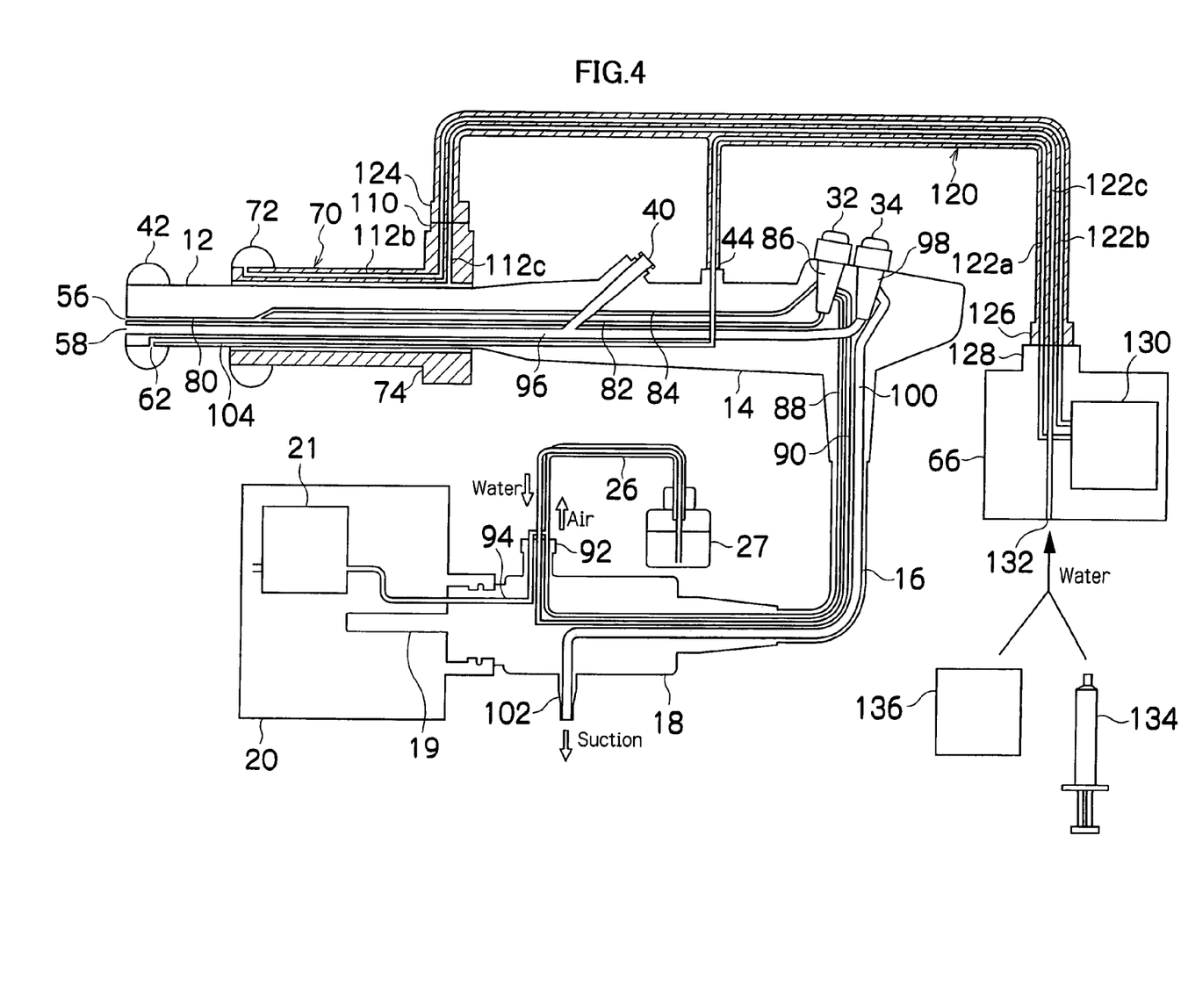
FIG. 4 is a configuration diagram of ducts in an endoscopic device having a different configuration from the configuration in FIG. 3.

The invention is not limited to the configuration of the first embodiment, but may have a configuration in which a first duct that communicates with a first balloon 42, a second duct that communicates with a second balloon 72, and a third duct through which a lubricant is supplied are correctively connected to one connector. For example, as shown in FIG. 4, a duct 122a only may be branched in the middle of a tube 120, and the branched portion is directly connected to a supply/suction port 44 of an endoscope 10.

Figure 5:
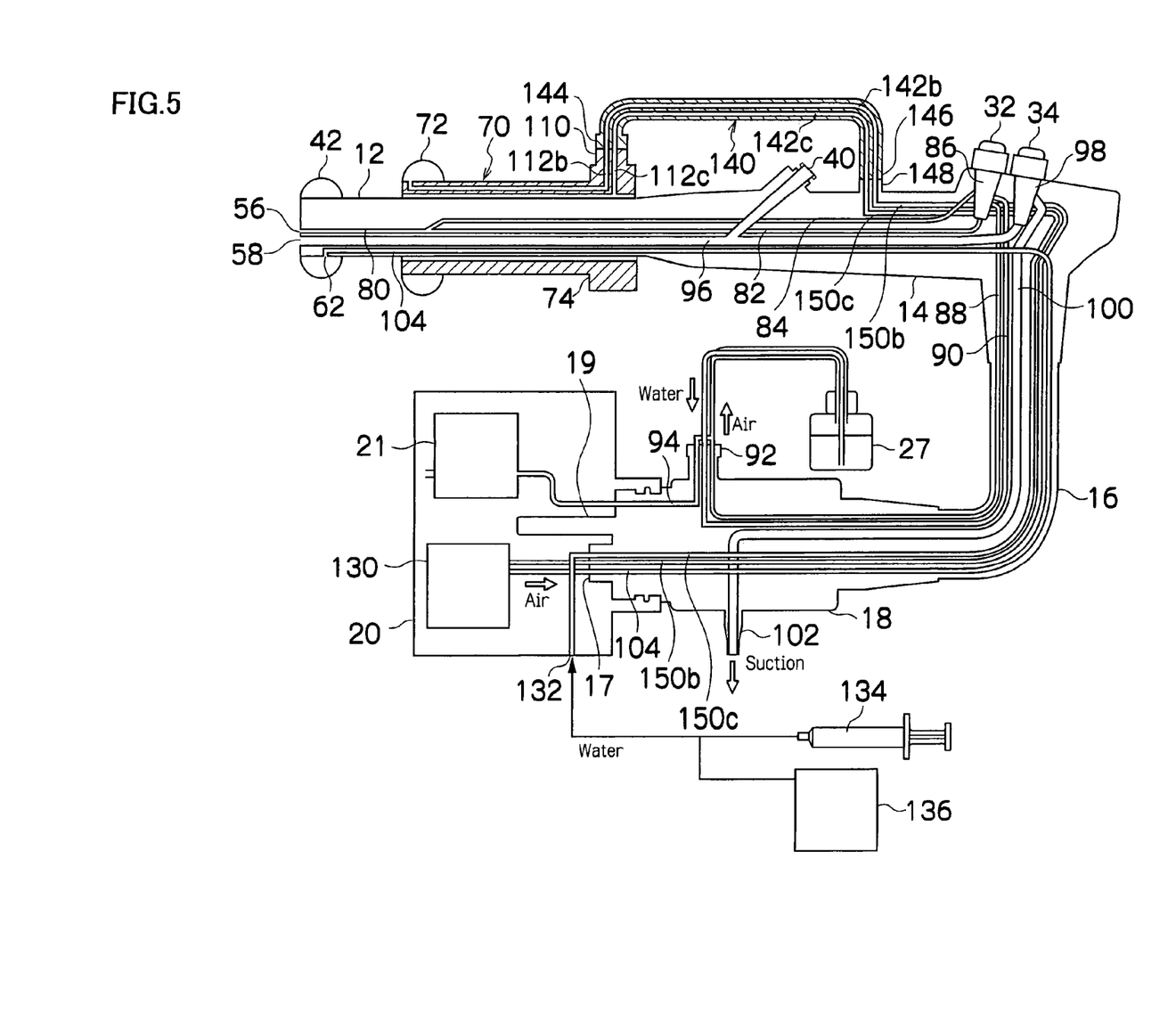
FIG. 5 is a schematic configuration diagram of ducts for a fluid according to a second embodiment.

FIG. 5 is a schematic configuration diagram of ducts for a fluid in an endoscopic device according to a second embodiment.

As shown in FIG. 5, ducts 112*b* and 112*c* are connected to a connector 110 of an insertion aid member 70. An end connector 144 of a tube 140 is connected to the connector 110. Two ducts 142*b* and 142*c* are formed in the tube 140, and the ducts 142*b* and 142*c* communicate with the ducts 112*b* and 112*c*, respectively. The other end connector 146 of the tube 140 is connected to a connector 148 of a hand operation portion 14. Tubes 150*b* and 150*c* are connected to the connector 148, and the tubes 150*b* and 150*c* communicate with the ducts 112*b* and 112*c*, respectively. The tubes 150*b* and 150*c* each are inserted through a universal cable 16, and extended to a connection surface 17 of an LG connector 18. A tube 104 that communicates with a first balloon 42 is extended to and placed in the connection surface 17.

A light source device 20 has a function of the balloon control device 66 in the first embodiment. Specifically, the light source device 20 incorporates an air pump 130 and has a lubricant injection port 132. When the LG connector 18 is connected to the light source device 20, the tube 104 and the tube 150*b* communicate with the air pump 130 to cause the tube 150*c* to communicate with the lubricant injection port 132.

According to the second embodiment configured as described above, the tubes 104, 150*b* and 150*c* are provided in the LG connector 18, and thus the tubes 104 and 150*b* communicate with the air pump 130 at the same time as the LG connector 18 is connected to the light source device 20 to cause the tube 150*c* to communicate with the lubricant injection port 132. This further facilitates connection of the connector.

Also, according to the second embodiment, a duct that communicates with the first balloon 42 (i.e. the tube 104), a duct that communicates with a second balloon 72 (i.e. the tube 150*b*), and a duct through which a lubricant is supplied (i.e. the tube 150*c*) are inserted through the universal cable 16, thereby preventing an increase in the number of cords drawn out of the hand operation portion 14 of an endoscope 10. This prevents reduction in operability of the hand operation portion 14 that occurs when the number of cords is increased.

In the second embodiment, the light source device 20 has the function of the balloon control device 66, but for example, the processor 30 in FIG. 1 may have the function of the balloon control device 66 as long as the device is an external device to which the endoscope 10 is connected. In this case, the three ducts (i.e. the tube 104, the tube 150*b*, and the tube 150*c*) are extended to the electric connector 24, and the electric connector 24 is connected to the processor 30 to connect the three ducts to the balloon control device 66. This facilitates connection of the connector.

Figure 6:
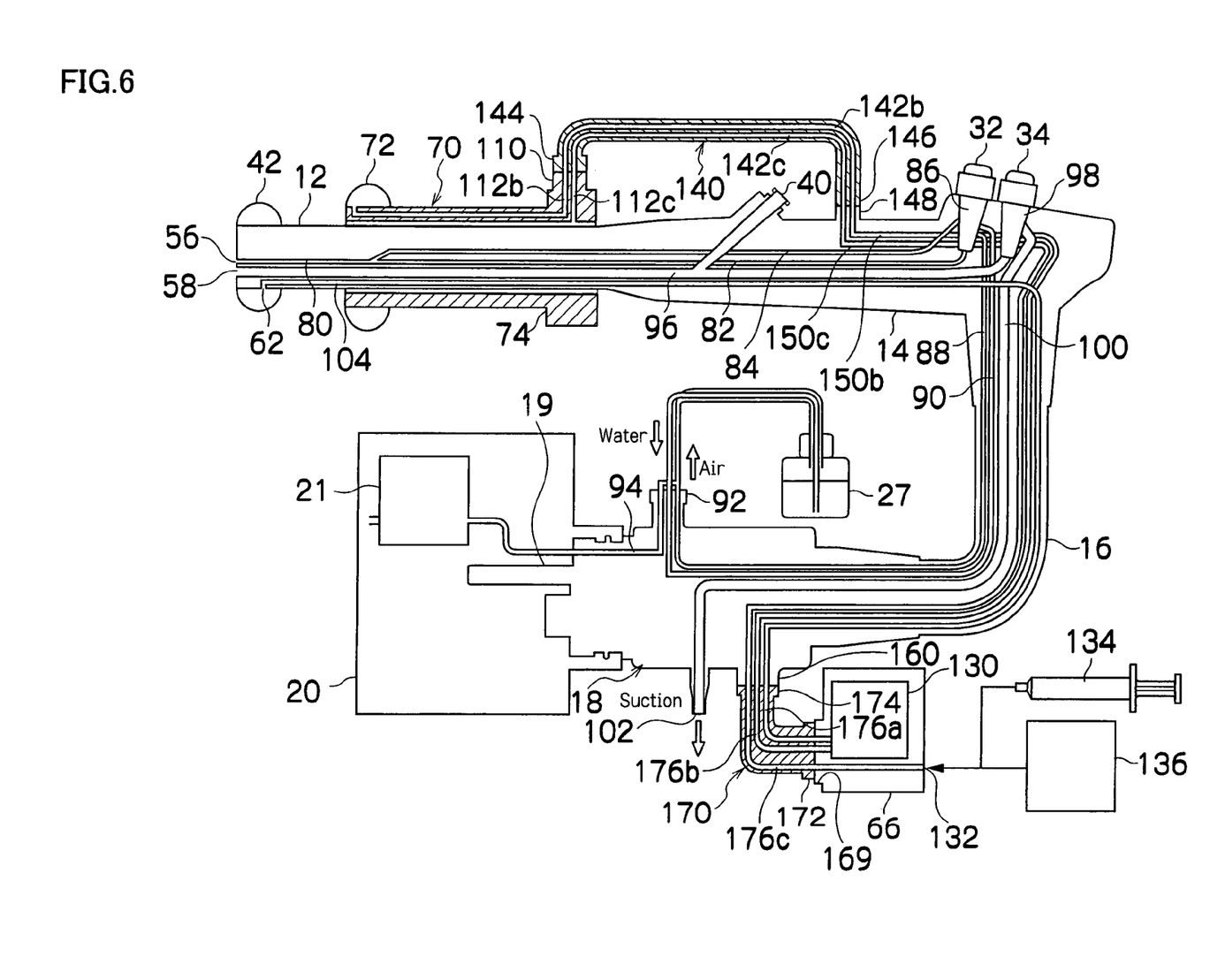
FIG. 6 is a schematic configuration diagram of ducts for a fluid according to a third embodiment.

FIG. 6 is a schematic configuration diagram of ducts for a fluid in an endoscopic device according to a third embodiment. In the third embodiment shown in FIG. 6, like the second embodiment shown in FIG. 5, a duct that communicates with a first balloon 42 (i.e. a tube 104), a duct that communicates with a second balloon 72 (i.e. a tube 150*b*), and a duct through which a lubricant is supplied (i.e. a tube 150*c*) are inserted through a universal cable 16, and extended to an LG connector 18. In the third embodiment, however, a connector 160 is formed in an outer surface of the LG connector 18, and the tubes 104, 150*b* and 150*c* are connected to the connector 160.

On the other hand, a balloon control device 66 is provided separately from a light source device 20, and the balloon control device 66 incorporates an air pump 130 and has a lubricant injection port 132. A connector 162 is provided in the balloon control device 66, and a connector 172 provided at one end of a tube 170 is connected to the connector 162. Then, a connector 174 provided at the other end of the tube 170 is connected to the connector 160 of the LG connector 18.

Three ducts 176*a*, 176*b* and 176*c* are formed in the tube 170, and the connector 174 is connected to the connector 160 to cause the three ducts 176*a*, 176*b* and 176*c* to communicate with the tubes 104, 150*b* and 150*c*, respectively. The connector 172 is connected to the connector 162 to cause the ducts 176*a* and 176*b* to communicate with the air pump 130, and cause the duct 176*c* to communicate with the lubricant injection port 132.

According to the third embodiment configured as described above, the tube 170 is simply connected to the LG connector 18 and the balloon control device 66 to allow the three ducts to be simultaneously connected, thereby facilitating connection of the connector and eliminating connection errors.

In the third embodiment, like the second embodiment, the three ducts are inserted through the universal cable 16, and a small number of cords are drawn out of a hand operation portion 14, thereby improving operability of the hand operation portion 14.

In the third embodiment, the three ducts are extended to the LG connector 18, but the present invention is not limited to this. That is, the ducts may be extended to a connector portion of an endoscope 10 connected to an external device. For example, the three ducts may be extended to the electric connector 24 in FIG. 1.

What is claimed is:

1. An endoscopic device, comprising:
    an endoscope having a first balloon at a tip of an insertion portion thereof;
    an insertion aid member that is placed over the insertion portion of the endoscope to guide insertion of the insertion portion into a body cavity, and has a second balloon at a tip thereof;
    a first connector that protrudes from an outer peripheral surface of the insertion aid member; and
    a balloon control device that controls supply and suction of a fluid into and from the first balloon and the second balloon,
    wherein a first duct that communicates with the first balloon, a second duct that communicates with the second balloon, and a third duct through which a lubricant is supplied between the insertion portion and the insertion aid member, the second duct and the third duct are connected to an opening formed in a bottom of the first connector, the first duct is connected to an opening formed in a side surface of the first connector via a port provided in a hand operation portion of the endoscope, and all three ducts being connected to the balloon control device via a single second connector provided on the balloon control device.

2. The endoscopic device according to claim 1, wherein the third duct is connected to a lubricant injection device via the connector.

3. The endoscopic device of claim 1, wherein the tip of the insertion portion of the endoscope further comprises:
    an observation optical system.

4. An endoscopic device, comprising:
    an endoscope having a first balloon at a tip of an insertion portion thereof;

a first connector that protrudes from an outer peripheral surface of an insertion aid member;

a second connector that is provided in a hand operation portion of the endoscope;

a tube whose end is connected to the first connector and the other end is connected to the second connector; and an insertion aid member that is placed over the insertion portion of the endoscope to guide insertion of the insertion portion into a body cavity, and has a second balloon at a tip thereof; and a balloon control device that controls supply and suction of a fluid into and from the first balloon and the second balloon, wherein the balloon control device is provided inside an external device to which a connector portion of the endoscope is connected, a first duct that communicates with the first balloon is connected to the connector portion, a second duct that communicates with the second balloon, and a third duct through which a lubricant is supplied between the insertion portion and the insertion aid member are connected to the connecter portion via the first connector, the tube and the second connector, and the connector portion is connected to the external device to connect at least the first duct and the second duct to the balloon control device via a single connector.

5. The endoscopic device of claim 4, wherein the tip of the insertion portion of the endoscope further comprises:

an observation optical system.

6. An endoscopic device, comprising: an endoscope having a first balloon at a tip of an insertion portion thereof; an insertion aid member that is placed over the insertion portion of the endoscope to guide insertion of the insertion portion into a body cavity, and has a second balloon at a tip thereof; a light source device that supply light to the endoscope; a balloon control device that controls supply and suction of a fluid into and from the first balloon and the second balloon and is provided separately from the light source device; a universal cable that is connected to a hand operation portion of the endoscope; a light guide connector that is provided at a tip of the universal cable and is connected to the light source device; a first connector that is formed in an outer surface of the light guide connector; and a second connector that is provided in the balloon control device and is connected to the first connector via a tube, wherein a first duct that communicates with the first balloon, a second duct that communicates with the second balloon, and a third duct through which a lubricant is supplied between the insertion portion and the insertion aid member are connected to the balloon control device via the universal cable, the light guide connector, the first connector, the tube and the second connector.

* * * * *